United States Patent [19]

Godfroid et al.

[11] 4,425,352
[45] Jan. 10, 1984

[54] SUBSTITUTED PHENOXYACETATES OF CYCLIC AMINES

[75] Inventors: Jean-Jacques Godfroid; Jean Thuillier, both of Paris, France

[73] Assignee: Agence Nationale de Valorisation de la Recherche, Paris, France

[21] Appl. No.: 256,168

[22] Filed: Apr. 21, 1981

[30] Foreign Application Priority Data

Apr. 30, 1980 [FR] France .................. 80 09885

[51] Int. Cl.³ ............... C07D 211/22; A61K 31/445
[52] U.S. Cl. ...................... 424/267; 546/238
[58] Field of Search .................. 546/222, 238; 260/326.47; 544/171; 424/248.55, 267, 274

[56] References Cited

U.S. PATENT DOCUMENTS

| | | | |
|---|---|---|---|
| 3,131,195 | 4/1964 | Rumpf et al. | 546/222 |
| 3,448,110 | 6/1969 | Griot et al. | 560/62 |
| 3,683,086 | 8/1972 | Griot | 424/244 |
| 3,708,587 | 1/1973 | Bencze | 424/317 |
| 4,072,754 | 2/1978 | Schacht et al. | 260/326.1 |
| 4,233,298 | 11/1980 | Mieville | 544/171 |

FOREIGN PATENT DOCUMENTS

| | | |
|---|---|---|
| 1359053 | 3/1964 | France . |
| 1359614 | 3/1964 | France . |
| 886437 | 1/1962 | United Kingdom . |

OTHER PUBLICATIONS

Thuillier et al., Bull. Soc. Chim. Fr. 1960, pp. 1786–1794.
Grenier et al., C.A. vol. 67, 1967 2900e.

*Primary Examiner*—Jane T. Fan
*Attorney, Agent, or Firm*—Hammond & Littell, Weissenberger and Muserlian

[57] ABSTRACT

The invention relates to substituted phenoxyacetates of cyclic amines.

These compounds are of the formula:

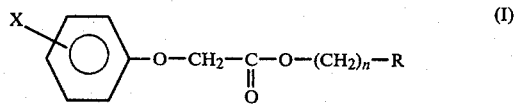

(I)

wherein
X is chlorine, fluorine or the trifluoromethyl radical
n is 0 or 1,
R is a cyclic amino group having five or six atoms possibly substituted on the nitrogen atom, the nitrogen of said amino group being in position 2 or 3 with respect to the oxygen or to the group $CH_2$ if present.

Application: treatment of obesities and hyperphagias, of cerebral and endocrinic deficiencies.

9 Claims, No Drawings

SUBSTITUTED PHENOXYACETATES OF CYCLIC AMINES

The present invention relates to new substituted phenoxyacetates of cyclic amines, a method for their preparation and applications thereof as medicaments.

There are already known substituted phenoxyacetate derivatives, and in particular dimethylaminoethyl 4-chloro-phenoxyacetate, which is currently called "Meclofexonate". This compound, which is used as a central metabolism regulator, was described in FR Pat. No. 1,359,614 and "special medicament" FR Pat. No. 398 M.

In FR Pat. No. 1,359,053 and "special medicament" FR Pat. No. 463 M as well as in the article by G. THUILLIER et al. in Bull. Soc. Chim. Fr. 1960, 1786–94, there were also described regulators of the central nervous system metabolism and especially derivatives of 4-chloro-phenoxyacetate, in particular piperidinoethyl 2-methyl-4-chloro-phenoxyacetate.

G. GRENIER et al. also described phenoxyacetates and their psychomimetic properties [Chim. Ther. 1966 (7) 408–14].

As references illustrating the state of the art, there may also be cited:

GB Pat. No. 886,437 relating to basic esters of etherified benzylic acids and their anti-cough properties;

U.S. Pat. No. 4,072,754 relating to hydratropic acid derivatives, viz. the derivatives of 2-phenyl-2-phenoxy-propionic acid, which are suitable to lower the cholesterol level;

U.S. Pat. No. 3,708,587 relating to hypocholesterolemic phenoxyaliphatic acids;

U.S. Pat. No. 3,683,086, which discloses acetic acid derivatives for treatment of hyperlipemia;

U.S. Pat. No. 3,448,110 relating to derivatives of isobutyric acid, suitable as hypocholesterolemic/hypolipemic agents;

FR Pat. No. 74,43,033 relating to substituted aryloxy- and arylthioalcanes and to the medicaments, possessing in particular hypocholesterolemic properties, containing such compounds.

Most of these references relates to products having hypocholesterolemic or hypolipemic properties. It will be noted that these products have a highly lipophilic aromatic structure and that usually the carbon between the oxygen and the ester function is substituted. These products are so lipophilic that they cannot get through the haemato-encephalic wall.

Now, there has been found a new series of chemical compounds which are remarkable stimulators of the central nervous activity, apt to counteract the disorders of the nerve cell and of its metabolism.

Moreover, the compounds of the invention are active against blood platelet clotting and have a diuretic activity.

The compounds according to the invention are substituted phenoxyacetates of cyclic amines of general formula:

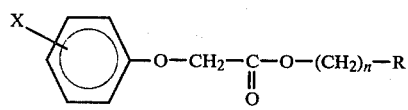
(I)

wherein:

X is chlorine, fluorine or the trifluoromethyl radical,
n is 0 or 1,
R is a cyclic amino group possibly substituted on the nitrogen atom, the nitrogen of said amino group being in 2 or 3 position with respect to the oxygen or to the group CH$_2$ if present, on the condition that when R is 3-(N-methylpiperidinyl) and n is zero, when X is chlorine, it is in the ortho or meta position.

As examples of cyclic amino groups suitable for the purposes of the invention, there may be cited piperidine, pyrrolidine and morpholine.

As preferred examples of amino-cyclic groups suitable for the purposes of the invention, there may be cited the groups of the following formulas:

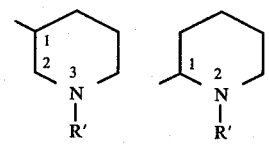

wherein R' is a lower alkyl group, such as methyl or ethyl group.

The present invention also relates to the pharmaceutically acceptable salts of the compounds of formula I.

The invention also has for its object a method for the preparation of the compounds of formula I. This method consists:

(1) in reacting the phenoxyacetic acid of formula

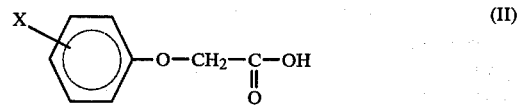
(II)

or a derivative thereof with a cyclic aminoalcohol of formula:

R—(CH$_2$)$_n$—OH     (III), and (2) in converting, if so required, the thus obtained compound into a pharmaceutically acceptable salt, X, R and n being such as defined above.

As examples of aminoalcohols of formula III suitable for the purposes of the invention, the following aminoalcohols may be cited: N-methyl-3-piperidinol, N-ethyl-3-piperidinol, N-methyl-piperidine-3-methanol and N-methyl-piperidine-2-methanol.

As derivatives of the acid, use may be made of an ester, the acid chloride or the anhydride.

Advantageously, there is used the chloride of the phenoxyacetic acid of formula II in an aliphatic or aromatic hydrocarbonaceous solvent, such as benzene, with solvent reflux. Preferably, use is then made of an excess of the aminoalcohol, the latter affording the binding of the hydrochloric acid formed. The product resulting from reaction of this chloride with the amine of formula III is thus a hydrochloride which may be converted by conventional means into the corresponding free amine, for instance by reaction with a carbonate.

The free amine thus obtained may be thereafter converted into a pharmaceutically acceptable salt by reaction with an acid currently used to produce pharmaceutically acceptable salts. Examples of suitable acids are maleic acid, fumaric acid, oxalic acid, succinic acid, citric acid and the like.

The compounds according to the invention have a regulating action on the nervous system, of metabolic origin; this regulating action involves modifications in the cerebral physiology, but also in the alimentary physiology, through a control on the hunger and thirst behaviours. It was found that the actions on the central nervous system of compounds of the invention are of the regulating and stimulating type, but without the exciting characteristics of Amphetamine.

The compounds according to the present invention are suited to correct defective cerebral and endocrinic metabolisms. In particular, the compounds of the invention may be used for the treatment of obesities and hyperphagias, of cerebral and endocrinal deficiencies.

Finally, the invention relates to pharmaceutical compositions containing, as active ingredients, a compound of formula I according to the invention in combination with a pharmaceutically acceptable carrier.

The pharmaceutical compositions according to the invention can be in the form of compositions for oral or parenteral, e.g. intra-veinous, administration.

The invention will now be described in more details in the following illustrative, non restrictive examples. For the sake of simplification, the synthetized compounds according to the invention are identified by the abbreviations PM 168, 169, 170 and 172.

EXAMPLE 1

Preparation of the hydrochloride of N-methyl-3-hydroxymethyl-piperidine (4-chloro-phenoxyacetate) (PM 170)

Parachlorophenoxyacetic acid chloride (68.33 g) was added, dropwise, to a solution of 100 cm³ of benzene and of N-methylpiperidine-3-methanol (86 g) cooled to 0° C. After the addition, the mixture was refluxed for two hours. After cooling to ordinary temperature, the reaction mixture was filtered on a Buchner, so as to remove the N-methylpiperidine-3-methanol hydrochloride formed. The filtrate was treated in a rotary evaporator so as to remove the benzene and the thus obtained oil was taken up with ether. This solution was repeatedly washed with water and the ethereal phase was dried on magnesium sulphate. The ether was then driven off in a rotary evaporator in a water bath at a temperature of about 60° C. so as to remove the water traces.

Once again, the oil obtained (70.6 g, yield=71.2%) was dissolved in anhydrous ether. In this solution, a stream of dry hydrochloric acid was bubbled. The hydrochloride precipitated and the reaction was stopped after vanishing of the starting amine and appearance of the hydrochloride. This was followed by chromatography on a thin silica layer; eluent:ethyl acetate.

The hydrochloride was carefully washed with ether then acetone, both anhydrous. Recrystallization was effected, once, in anhydrous alcohol. There was obtained 68.4 g of PM 170; yield: 61.4% M.P.=179° C. (capillary).

Analysis: $C_{15}H_{21}Cl_2NO_3$

|  | C | H | N | Cl |
|---|---|---|---|---|
| Calculated: | 53.89 | 6.28 | 4.19 | 21.25 |

| -continued |  |  |  |  |
|---|---|---|---|---|
|  | C | H | N | Cl |
| Found: | 54.15 | 6.44 | 4.31 | 21.20 |

Infrared (in KBr): function at 1730 cm$^{-1}$.

NMR, δ (ppm), DMSOd6 characteristic peaks: 2.72 singlet (N$^+$—C$\underline{H}_3$); 4.17, doublet (—O—C$\underline{H}_2$— piperidine); 4.93 singlet $$(O-CH_2-\underset{\underset{O}{\parallel}}{C}-).$$

Mass spectrography: ion-M+ molecular radical at m/e 297 (334—HCl—H), at m/e 186, the fragment (Cl—⟨phenyl⟩—O—CH₂C(=O)—O⁺)

is noted.

EXAMPLE 2

The procedure described in Example 1 was repeated with the mere exception that there was used, instead of N-methyl-piperidine-3-methanol, one of the following aminoalcohols:
N-methyl-3-piperidinol;
N-ethyl-3-piperidinol;
N-methyl-piperidine-2-methanol
and there was obtained, respectively, the following products, for which the physical characteristics of the respective hydrochlorides are set forth in Table I: N-ethyl-3-piperidine 4-chloro-phenoxyacetate (PM 168), N-methyl-2-hydroxymethyl-piperidine 4-chloro-phenoxyacetate (PM 172).

TABLE 1

| N° | Melting point (capillary) °C. | Analysis Calculated % | Found % | Ion-M+ radical |
|---|---|---|---|---|
| PM 168 | 169.5 | C 53.89 | 53.04 | 297 |
|  |  | H 6.28 | 6.35 |  |
|  |  | N 4.19 | 4.48 |  |
|  |  | Cl 21.25 | 21.39 |  |
| PM 172 | 192 | C 53.89 | 54.05 | 297 |
|  |  | H 6.28 | 6.39 |  |
|  |  | N 4.19 | 4.44 |  |
|  |  | Cl 21.25 | 21.37 |  |

EXAMPLE 3

The procedure described in Example 1 was repeated, using as starting products parafluorophenoxyacetic acid chloride and N-methyl-3-piperidinol.

The N-methyl-3-piperidine (4-fluorophenoxyacetate) (PM 243) having the formula was obtained:

F—⟨phenyl⟩—O—CH₂—C(=O)—O—⟨piperidine-N-CH₃⟩, HCl having a melting point of 194° C. on a Köpfler bench after re-crystallization in acetonitrile.

The analysis of the product obtained gave the following results:

| Analysis: | C | H | N | Cl |
|---|---|---|---|---|
| Calculated: | 55.36 | 6.30 | 4.61 | 11.67 |
| Found: | 55.42 | 6.45 | 4.62 | 11.51 |

EXAMPLE 4

Pharmacological tests

The compounds of the invention obtained according to the above examples 1 and 2 were subjected to different pharmacological and toxicological tests.

The results obtained were compared with those of "Meclofenoxate" which is dimethylaminoethyl 4-chlorophenoxyacetate having the following formula:

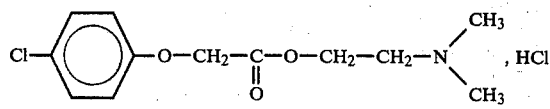

TEST A

Toxicity of the compounds of the invention and of Meclofenoxate

The toxicities were calculated according to the LITCHFIELD and WILCOXON method (J. Pharm. and Exp. Therap. 1949, 96, p. 99, 113).

The products were administered per os and per intraveinous route to mice.

The results are reported in Table II hereunder.

TABLE II

| Products | Toxicities | |
|---|---|---|
| | LD 50 P.O. mg | LD 50 I.V. mg |
| Meclofenoxate | 1750 | 350 |
| PM 168 | 1800 | 140 |
| PM 170 | 2300 | 175 |
| PM 172 | 1500 | 160 |

It may be seen that the compounds of the invention substantially all have toxicities of the same order of magnitude. Tolerance thereof seems good when the survivors are monitored over several days.

The PM 170 product is less toxic than "Meclofenoxate" 0 per os route.

TEST B

Actions on the central nervous system (1) Action on the fish chromatophores

The physiology of fish chromatophores is dependent on hypothalamic secretions of the lower portion of the diencephalon. The psychotropic and cerebral-orientation drugs can modify the physiology of these regions [J. Thuillier et al. C.R. Soc. Biol. 1961, 155.10, p. 1924–1928]. This test is known to evidence the action of the products on the diencephalon which controls distension and blackening of fish chromatophores.

Use is made of the Phoxinus Phoxinus Linné as immersed in an aquarium containing a selected concentration of one of the compounds of the invention prepared according to Examples 1 and 2. The time for the fish blackening to occur was measured. The same test was effected with Meclofexonate. The results obtained are shown in Table III hereunder.

TABLE III

| Product | Minimum effectual concentration | Time of occurrence of the blackening in seconds |
|---|---|---|
| PM 168 | 0.03 per 1000 | 30 |
| PM 170 | 0.05 per 1000 | 90 |
| PM 172 | 0.05 per 1000 | 60 |
| Meclofenoxate | 0.25 per 1000 | 90 |

The results in Table III above show that the compounds of the invention are more active than "Meclofexonate"; they are 3 to 25 times more active as regards the dosage, but also render the occurrence of blackening more rapid.

(2) Actions on cerebral oedema of rats

The alkylated tin compounds are toxic and cause selective oedema of the central nervous system and in particular of the brain (Works of R. KATZMAN et al. Arch. Neurol. 9, 178, 1963). The water content of the cerebral tissue is increased. Similarly, the cerebral sodium content increases, while the potassium is reduced.

It was found that at a dosage of 50 mg per kilogram, the pM 168, 170 and 172 considerably reduce the occurrence of the oedema caused by ingestion of triethyltin chloride, counteract the loss of $K^+$ and limit the build up of $Na^+$. 100 mg per kg of Meclofenoxate are required to provide the same result.

(3) Orientation test after an electroshock in rats

This test consists in causing a loss of orientation and motive disorders in rats after repetition of 4 series of electroshock [M. Hérold: Acta. Int. Meet. Psycho. Drug. 1960].

The PM 170 was slightly effective at a dosage of 100 mg on the first 2 series of electroshock.

Meclofenoxate is absolutely inefficient up to a dosage of 200 mg/kg.

(4) Action on hunger behaviours

Hunger and thirst regulation is dependent on stimulating secretions from the hypothalamus. These regulator centers may be disturbed either in acquired manner in genetically obese animals, either consequently to the destruction of the involved centers by selective poisons, such as aurothioglucose.

Aurothioglucose tests on mice

If 250 mg/kg of aurothioglucose are injected to mice, then the cells of the hypothalamic nuclei will degenerate and cause an hyperphagia syndrome in animals which is evidenced by:

a distension of the stomach,
a considerable increase in ponderal growing.

A. Protective effect of the products of the invention against the action of aurothioglucose The mice were treated with one of the products of the invention ½ hour before the intraperitoneal injection of aurothioglucose (250 mg/kg).

The PM 168, 170, 172 products according to the invention thus administered to the animals counteract both hyperphagia and the weight gain of mice intoxicated with aurothioglucose as shown by the results in Table IV hereafter:

TABLE IV

| Code | Dose mg/kg P.O | Number of animals | Decrease in the stomach weight With respect to the aurothioglucose reference | Degree of significance | |
|---|---|---|---|---|---|
| PM 168 | 100 | 18 | 2.5510 | P | <0.02 |
|  | 150 | 12 | 3.37 | P | <0.01 |
| PM 170 | 20 | 12 | 3.2155 | P | <0.01 |
|  | 50 | 12 | 2.8729 | P | <0.01 |
|  | 100 | 18 | 4.2287 | P | <0.01 |
| PM 172 | 60 | 12 | 2.6299 | P | <0.02 |
|  | 100 | 6 | 2.2727 | P | <0.05 |
| Meclo-fenoxate | 250 | 12 | 2.2495 | P | <0.05 |
|  | 300 | 12 | 1.6129 | NS |  |

The results in Table IV show that PM 170 which, as all the products of the invention, counteracts the increase of the stomach weight distension, has a very high activity.

The Meclofenoxate is only active at a dosage of 250 mg/kg, i.e. it is 12.4 times less active than PM 170.

At last, if monitoring the evolution of the weight gain curve for mice treated with aurothioglucose, it will be found that 15 days after the beginning of the experimentation:
- the mice treated with aurothioglucose have a weight increased by 49%;
- the mice treated with aurothioglucose plus Meclofenoxate have a weight increased by 45%;
- the mice treated with aurothioglucose plus PM 170 have a weight increased by 34%.

Still there, Meclofenoxate is less active than PM 170 to counteract obesity caused by aurothioglucose.

B. Curative action of PM 170 and of Meclofenoxate after development of obesity under the action of aurothioglucose Mice were rendered obese by intra-peritoneal injections of aurothioglucose (800 mg/kg).

After the development of obesity, a plateau was obtained in the weight curve. There was then selected an homogenous group of mice and treatment with PM 170 and Meclofenoxate was initiated. The results obtained were compared with a group of reference mice treated only with aurothioglucose (ATG controls).

PM 170 at doses of 200, 100 and 50 mg/kg per day during 18 days, per os, caused a weight drop/ATG controls of 14%, 12% and 5%, respectively.

As regards alimentary consumption, the decrease was of 36% at 200 mg/kg and 33% at 100 mg/kg.

The decrease in alimentary consumption is of 23 to 26% respectively for doses of 200 and of 100 mg/kg of Meclofenoxate.

In conclusion, the activity of PM 170 is markedly higher than Meclofenoxate at 200 mg/kg. It has the same activity at 50 mg/kg than Meclofenoxate at 200 mg/kg.

| Dose in mg/kg | 200 | 100 | 50 |
|---|---|---|---|
| Decrease in weight/Aurothioglucose references: | | | |
| PM 170 | 14% | 12% | 5% |
| meclofenoxate | 5% | 10% | inactive |
| Decrease in aliment consumption/ATG references | | | |
| PM 170 | 36% | 33% | 10% |
| Meclofenoxate | 22.9% | 26% | inactive |

Action of the products of the invention on genetically obese mice

On genetically obese mice (of a weight of 42-42.5 g), the PM 170 product is active both on alimentary consumption and on weight development as shown by the results in Table V.

TABLE V

Activity of PM 170 and of Meclofenoxate on genetic obesity of male and female mice

| Animals | Products | Alimentary consumption | Weight |
|---|---|---|---|
| Treated obese males |  | 4.384 ± 0.886 | 39.3 ± 0.882 |
| Obese male controls | PM 170 | 6.786 ± 0.853 | 43.3 ± 0.284 |
| Treated normal males | 200 mg/kg | 4.716 ± 0.880 | 22.22 ± 0.484 |
| Normal male controls |  | 6.307 ± 0.746 | 25.34 ± 0.365 |
| Treated obese females |  | 5.542 ± 0.302 | 41.2 ± 0.802 |
| Obese female controls | Meclofenoxate 300 mg/kg | 6.347 ± 0.637 | 42.5 ± 0.787 |
| Treated normal females |  | 5.842 ± 0.842 | 24.8 ± 0.602 |
| Normal female controls |  | 6.703 ± 0.597 | 25.3 ± 0.504 |

Finally, gastric ingestion during 18 days of 200 mg/kg of PM 170 causes, in obese mice, a steady decrease in weight of 8.3%, while in the same conditions there occurs, with Meclofenoxate, a decrease in weight of 2.2%.

TEST C

Effect against blood platelet clotting

All the products of the invention prepared according to Examples 1 and 2 at a dose of 10 mg/kg have an effect against plaquette aggregation which was observed on the pia-mater vessels of rabbits [M. M. G. BOZEIX 7th. Int. Congress of Pharmacology, Paris, July 1978].

Moreover, PM 170, at a dose of 100 mg/kg, has a slight diuretic action.

It should be noted that Meclofenoxate has no effect against blood platelet clotting nor diuretic action.

By way of indication, it may be mentioned that PM 170 may be used at daily doses of about 0.05 to 1.00 g per day, in unit dosage of 0.01 to 0.25 g per pharmaceutical species.

The solutions for intra-veinous injection may be prepared at concentrations from 5 to 10%.

It should be noted that among the compounds of the invention which were tested, PM 170 has remarkable properties; it is from five to twelve times more active than Meclofenoxate as regards the action of the latter on the central nervous system, and 5 to 10 times better than the latter as regards the action on hunger and thirst.

We claim:

1. A compound selected from the group consisting of an amine of the formula

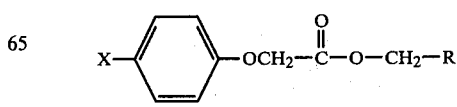

wherein X is selected from the group consisting of chlorine, fluorine and —CF$_3$ and R is a piperidine with the nitrogen atom being in the 2- or 3-position with respect to the —CH$_2$— group and being optionally substituted on the nitrogen atom with lower alkyl or a non-toxic, pharmaceutically acceptable acid addition salt thereof.

2. A compound of claim 1 selected from the group consisting of the 4-chloro-phenoxy-acetate of N-methyl-3-hydroxymethyl-piperidine and N-methyl-2-hydroxymethyl-piperidine or a non-toxic, pharmaceutically acceptable acid addition salt thereof.

3. A compound of claim 2 in the form of its hydrochloride salt.

4. An appetite suppressing composition comprising an effective appetite suppressing amount of a compound of claim 1 and a pharmaceutical carrier.

5. A composition of claim 4 wherein the active compound is selected from the group consisting of the 4-chlorophenoxyacetate of N-methyl-3-hydroxymethyl-piperidine or a non-toxic, pharmaceutically acceptable acid addition salt thereof.

6. A method of suppressing appetite in warm-blooded animals comprising administering to warm-blooded animals an effective appetite suppressing amount of a compound of claim 1.

7. A composition of claim 4 wherein the active compound is selected from the group consisting of the 4-chlorophenoxyacetate of N-methyl-2-hydroxymethyl-piperidine or a non-toxic, pharmaceutically acceptable acid addition salt thereof.

8. The method of claim 6 wherein the active compound is selected from the group consisting of the 4-chlorophenoxyacetate of N-methyl-3-hydroxymethyl-piperidine or a non-toxic, pharmaceutically acceptable acid addition salt thereof.

9. The method of claim 6 wherein the active compound is selected from the group consisting of the 4-chlorophenoxyacetate of N-methyl-2-hydroxymethyl-piperidine or a non-toxic, pharmaceutically acceptable acid addition salt thereof.

* * * * *